(12) United States Patent
Park et al.

(10) Patent No.: US 7,063,976 B2
(45) Date of Patent: *Jun. 20, 2006

(54) PROCESS FOR PREPARING BETA-FRUCTOFURANOSIDASE ENZYME AND A PROCESS FOR PRODUCING FRUCTOOLIGOSACCHARIDES

(75) Inventors: Yong Kun Park, Campinas (BR); Gláucia Maria Pastores, Campinas (BR)

(73) Assignee: Usina da Barra S/A—Acucar e Alcool, Barra Bonita-SP (BR)

(*) Notice: Subject to any disclaimer, the term of this patent is extended or adjusted under 35 U.S.C. 154(b) by 190 days.

This patent is subject to a terminal disclaimer.

(21) Appl. No.: 10/196,440

(22) Filed: Jul. 15, 2002

(65) Prior Publication Data

US 2002/0182682 A1 Dec. 5, 2002

Related U.S. Application Data

(60) Division of application No. 09/535,510, filed on Mar. 24, 2000, now abandoned, which is a continuation of application No. 09/194,456, filed as application No. PCT/BR98/00022 on Mar. 24, 1998, now abandoned.

(30) Foreign Application Priority Data

Mar. 25, 1997 (BR) .................................... 9700452

(51) Int. Cl.
*C08B 37/00* (2006.01)
*C12N 1/14* (2006.01)
*C07G 11/00* (2006.01)
*C07H 1/00* (2006.01)
*C07H 1/06* (2006.01)

(52) U.S. Cl. ...................... 435/274; 435/814; 435/913; 435/254.3; 536/16.9; 536/1.11; 536/123.1; 536/127

(58) Field of Classification Search ................ 435/913, 435/814, 274, 254.3; 536/1.11, 16.9, 123.1, 536/127; 530/823, 820, 412, 350
See application file for complete search history.

(56) References Cited

U.S. PATENT DOCUMENTS 6,337,201 B1 * 1/2002 Yanai et al. ................. 435/200

OTHER PUBLICATIONS

Hidaka et al. Agric. Biol. Chem. 52: 1181-1187, 1988.*
Lahoz et al. Z. Mikrobiol. 23: 17-25, 1983.*
Wallis et al. Arch. Biochem. Biophys. 345: 214-222, 1997.*
Ukhina et al. News from Institutes of Higher Education, Food Technology, 3-4: 33-34, 1996.*
Korneeva et al. Biochemistry (Moscow) 63 (10): 1220-1225, 1998.*
Srinivas et al. Chem. Mikrobiol. Technol. Lebensm. 15 (1-2):41-46, 1993.*
Park et al. World J. Microbiol. Biotechnol. 7,3: 331-334, 1991.*
Rubio et al. Curr. Microbiol. 31: 80-83, 1995.*
Hirayama et al. Agr. Biol. Chem. 53: 667-673, 1989.*
Ukhina E. Yu et al., "Sunstantiation of parameters of biosynthesis and Nb-fructofuranosidase use in pastry production," *Izvestiya Vysshikh Uchebnykh Zavedenii, Pishchevaya Teknologiya* (1996) (English language abstract).
Srinivas et al., "Growth kinetics, Na-galactosidase biosynthesis, and concomitant production of invertase by *Aspergillus niger* NCIM 839 in solid state fermentation system" (1993) (English language abstract).
Srinivas et al., "Growth kinetics, Na-galactosidase biosynthesis, and concomitant production of invertase by *Aspergillus niger* NCIM 839 in solid state fermentation system," *Chemie Mikrobiologie Technologie Der Lebensmittel*, vol. 15, No. 1/2: 41-46 (1993).
Zhiying Peng et al., "Study on selection and properties of a high fructooligosaccharide-producing beta-fructofuranoside activity *Aspergillus niger*," *Chemical Abstracts* 127 (1997) (English language abstract).
Dan. V et al., "Preparation of fungus invertase, useful for manufacture of invert sugar by selective breeding fo *Aspergillus niger* medium comprising mineral salts and starch in static cultures," RO-107684 (1993).
L.M. Boddy et al., "Purification and characterisation of an *Aspergillus niger* invertase and its DNA sequence," *Current Genetics* 24:60-66 (1993).

(Continued)

Primary Examiner—S. Devi
(74) Attorney, Agent, or Firm—Darby & Darby

(57) ABSTRACT

A process for preparing beta-fructofuranosidase enzyme and a process for producing fructooligosaccharides, in which the preparation of the enzyme is obtained by cultivating the fungus *Aspergillus niger*, either wild or mutated, in a preferably semi-solid culture medium, in order to produce an extracellular enzyme, which is submitted to transfructosylation for producing fructooligosaccharides comprising sugars which are formed by one unit of sucrose and by two, three and four units of fructose.

3 Claims, No Drawings

OTHER PUBLICATIONS

M. Hirayama et al., "Purification and properties of a Fructooligosaccharide-producing β-Fructofuranosidase from *Aspergillus niger* ATCC 20611," *Agricultural and Biological Chemistry* 53, No. 3: 667-673 (1989).

O. Schmidt et al., "Experimental and theoretical investigations of submerged fermentation and synthesis of pectinolytic enzymes by *Aspergillus niger*," *Applied Microbiology and Biotechnology* 43: 424-430 (1995).

* cited by examiner

PROCESS FOR PREPARING BETA-FRUCTOFURANOSIDASE ENZYME AND A PROCESS FOR PRODUCING FRUCTOOLIGOSACCHARIDES

This is a division of application Ser. No. 09/535,510, filed Mar. 24, 2000, now abandoned, which is a Continuation of Ser. No. 09/194,456, filed Nov. 23, 1998, now abandoned which was a U.S. National Phase of International Application No. PCT/BR98/00022, filed Mar. 24, 1998. Each of these prior applications is hereby incorporated herein by reference, in its entirety.

FIELD OF THE INVENTION

The present invention refers to a process for preparing beta-fructofuranosidase enzyme obtained from the culture of fungi of the *Aspergillus niger* species, of both the wild and mutated types, and its use in the production of fructooligosaccharides.

BACKGROUND OF THE INVENTION

Fructooligosaccharides are sugars found in nature, which, when consumed, provide several benefits to the health of a person.

GF2 (1-kestose), GF3 (nystose) and GF4 (fructofuranosil nystose) are composed of glucose units, to which are bound one, two or even four fructose units.

These sugars can be found in a large quantity of foods provided by nature, such as asparagus, banana, garlic, onion, tomato or wheat. Besides giving a sweetish flavor to foods, they are neither cariogenic nor caloric and promote the population growth of the bifidus bacteria in the intestine, which reduce the activity of the putrefactive bacteria, thereby reducing the development of toxic products by fermentation.

In view of the benefits described above, the interest for fructooligosaccharides have raised progressively. Consequently, intensive investigations are now being undertaken with the aim of obtaining these fructooligosaccharides from enzymes. It is known that the beta-fructofuranosidase enzyme, which is used in the production of fructooligosaccharides by transfer activity can be obtained in different ways, particularly from the cultures of fungi of different species, such as *Aspergillus, Pennicillium, Fusarium, Gloesporium*, from the cultures of yeasts, such as Saccharomyces, Rhodotorulla, Pichia, Hansenula, Candida and Aureobasidium, and also from some plants, such as asparagus. It is also known that this enzyme may be prepared in different ways and under different process conditions. Said enzyme is also known for promoting the catalyzation of the transfructosylation reaction, which is responsible for transferring the fructosyl group from a donor to a receptor, which may be sucrose or a fructooligosaccharide, such as kestose, nystose, etc. Nevertheless, the structure of this enzyme is still unknown.

The manner by which the transfructosylation of the *Aspergillus orizac* occurs has been studied before, regarding its performance in the formation of fructose oligomers, by using sucrose as raw material.

It has been observed that the hydrolysis of sucrose with extracts of *Pennicillium spinulosum* was initially fast and followed by the formation of non-reducing fructooligosaccharides. The hydrolysis of these fructooligosaccharides occurred by transferring the fructose units to the water and eventually resulted in the complete hydrolysis of the sucrose. The transfructosylation and inversion activities occurred from the use of the same enzyme, i.e., the beta-fructofuranosidase (Bealing et al., *Biochem J* 53(2):277–285 (1953); Bealing, *Biochem J* 55(1):93–101 (1953)). From U.S. Pat. No. 4,849,356 fructooligosaccharides were produced with mycelium extracts, by culturing the fungus *Aspergillus phoenics* in an adequate culture medium. According to this document, the enzyme is preferably prepared on a solid substrate mostly containing sucrose. The beta-fructofuranosidase enzyme thus obtained is cell-bound and requires, to be recovered, complex operations for separating the mycelium from the liquid phase. In this prior art process, in order to obtain a good yield, the presence of sucrose is still required in the culture medium. Moreover, the enzyme obtained as described above provides only the formation of lower fructose oligomers, such as GF2, GF3, with the production of GF4 not being demonstrated.

The formation of fructooligosaccharides has also been investigated, by using cell suspension of several other fungi. Among these fungi, the *Aspergilus niger* ATCC 20611 produced the highest level of the activity of the beta-fructofuranosidase enzyme, as compared to the activity of hydrolysis (Hidaka et al, *Agric Biol Chem*, 52(5):1181–1187 (1988)). The enzyme was subsequently purified and then characterized.

DISCLOSURE OF THE INVENTION

In view of the results of these studies, which demonstrated a certain complexity regarding the preparation of the beta-fructofuranosidase enzyme, it is an object of the present invention to provide a process for preparing the beta-fructofuranosidase enzyme, which permits a yield in the range from 57% to 60% to be obtained.

It is also an object of the present invention to provide a process which is easy to carry out and of low cost, by using the enzyme in the free form.

It is still an object of the present invention to produce fructooligosaccharides, including not only GF2, GF3, but also GF4.

These and other objectives are attained by the provision of a process for preparing beta-fructofuranosidase enzyme, comprising the steps of:
a) inoculating the spores of the fungus *Aspergillus niger* in an adequate liquid or semi-solid culture medium;
b) cultivating the already inoculated fungus, in order to promote its growth with the formation of mycelium and the production of the beta-fructofuranosidase enzyme; and
c) separating the beta-fructofuranosidase enzyme from the mycelium and from the culture medium. The process further comprises incubating the fungus at a temperature of 30° C. for a period of 96 to 120 hours.

This new fungus, which is called *Aspergilus niger* 489, has been selected from a bank of microorganisms with more than 2,000 different strains of the Biochemistry Laboratory of FEA UNICAMP (Food Engineering School of the University of Campinas, Sao Paulo, Brazil), for it showed high efficiency in the production of the beta-fructofuranosidase enzyme and the consequent transfer of sucrose into a fructooligosaccharide (about 60% conversion), and it was submitted to a genetic mutation process with the drug N-nitrous-nitroguanidine and ultraviolet radiation for productivity increase. *Aspergillus niger* 489 was deposited on Mar. 5, 2003 with the American Type Culture Collection (ATCC), 10801 University Boulevard, Manassas, Va. 20110-2209, under the provisions of the Budapest Treaty on the International Recognition of the Deposit of Microorganisms for the Purposes of Patent Procedure, and was assigned ATCC Patent Deposit Designation No. PTA-5032.

The preparation of the enzyme may consist of an extract with no cells or with broken cells, or a purified extract of dry and concentrated cells. The enzyme may also be purified and concentrated from cells and culture medium, in which case there may or may not be used specific systems for breaking the cells when the use of the intracellular fraction is desired.

The preparation of the present beta-fructofuranosidase may be achieved in a liquid culture medium, which preferably contains 5% of sucrose, 1% of yeast extract, 1% of peptone and 0.3% of sodium chloride. Nevertheless, such procedure causes the production of intracellular enzyme in relation to the mycelium. Thus, although the *Aspergillus niger* 489 allows a high yield to be obtained in the production of the beta-fructofuranosidase enzyme, its separation process is industrially complex, requiring a certain number of operations for the final extraction of the enzyme.

For preparing the enzyme on a semi-solid substrate, all is needed is the presence of a cereal bran, preferably wheat bran, in the culture medium, the substrate being incubated at a temperature in the range of 25 to 40° C., during a period of about four to ten days.

Although the wheat bran has been mentioned as the preferred material for the formation of the semi-solid culture medium, it is important to point out that other brans from cereals containing starch, fibres and proteins may be used together with mineral salts and humidity.

It has been verified as adequate a culture medium in which its solid phase is formed of about 98% of cereal bran, preferably wheat bran, and 2% of mineral salts, such as magnesium sulfate, calcium chloride and potassium phosphate, the semi-solid culture medium consisting of about 40% of said solid phase and water as the remaining part.

The enzyme obtained according to the above cited procedure is not cell-bound, being in the free form and therefore determining the possibility of working with the immobilized beta-fructofuranosidase. The enzyme thus obtained can be easily separated.

It is important to point out, however, that the fungus *Aspergillus niger* may be cultivated on any other substrate, such as for example in a solid culture medium and in various other forms, such as containing or not containing sucrose in the culture medium. For instance, for the preparation of the enzyme in a solid medium, the fungus is pre-cultivated on a substrate composed of a P.D.A. (Potato, Dextrose, Agar) medium, which is sterilized for 20 minutes at 110° C. during four days. It should be noted, however, that the most economical procedure is the one which employs the semi-solid culture medium.

In order to obtain good results, the present beta-fructofuranosidase can be used in the production of frutooligosaccharides consisting of one unit of glucose and two, three and four units of fructose, with a a good development in a pH ranging from 5.0 to 9.5. The beta-fructofuranosidase activity reaches its maximum values in a pH ranging from 6.0 to 8.5. According to the U.S. Pat. No. 4,317,880, in the transfructolyation process which employs the beta-fructofuranosidase enzyme recovered from the culture medium containing *Pullularia pullulans*, the pH must be between 6.3 and 6.7. Yeasts cultures are usually more difficult to be processed, besides being more difficult to be filtered.

The thermal stability of the enzyme preparations derived from yeasts is also lower. For example, at high temperatures, the activity of this type of enzyme preparation decreases more rapidly than the activity of the enzyme preparations derived from fungi. Thus, the utilization of enzymes derived from fungi, more specifically the preparations of the present beta-fructofuranosidase enzyme, which derives from cultures of the fungus *Aspergillus niger*, are more adequate at higher temperatures.

As mentioned hereinbefore, the present beta-fructofuranosidase differs from other beta-fructofuranosidases derived from fungi also for presenting a better thermal stability. This means that, at rising temperatures, the activity of the present enzyme is diminished, as compared to other beta-fructofuranosidase enzymes. High temperatures are optimum for the preparation of fructooligosaccharides, with the optimum temperatures for preparing the fructosylation with the present beta-fructofuranosidase ranging between 40° C. and 65° C. Therefore, with the adequate choice for the process conditions, which can be easily determined, the transfructosylation can be carried out, without occurring any infection of the reaction mixture.

The immobilization of the present beta-fructofuranosidase may be desirable, even though partially, for several other purposes, such as, for example, in the utilization in a fixed or fluidized bed. As already described, the immobilization of the enzyme can be obtained by employing the semi-solid substrate containing wheat bran or a bran from any other cereal.

Another variable characteristic of the present beta-fructofuranosidase is that not only GF2 (kestose) and GF3 (nystose) are formed, but also GF4 (fructofuranosil nystose) during the reaction. Due to the low invertase activity of the present enzyme, the inversion of sugars continues to be very low, resulting in the formation of a certain amount of glucose.

The concentration of sucrose also exhibits a wide range of variation, from 25% to 80% (m/m), in which the enzyme activity occurs, with the highest activity values occurring in the range of 40% to 70% (m/m) of sucrose concentration. The sucrose used may be in the pure form or that contained in intermediate molasses of the sugar refining process and the reaction mixtures, which are obtained in the transfructosylation of sucrose, can be analyzed by high pressure liquid chromatography (HPLC).

What is claimed is:

1. A process for producing fructooligosaccharides comprising 1-kestose (GF2), nystose (GF3), and fructofuranosil nystose (GF4), comprising the steps of
   a) inoculating the spores of the fungus *Aspergillus niger* 489 having the deposit designation of PTA-5032 in a liquid or semi-solid culture medium;
   b) cultivating the inoculated fungus of step (a), in order to promote the growth of said fungus with the formation of mycelium and the production of beta-fructofuranosidase enzyme;
      wherein said fungus is incubated at a temperature of 30° C. for a period of 96 to 120 hours;
   c) separating the beta-fructofuranosidase enzyme from the mycelium and from the culture medium; and
   d) transfructosylating the beta-fructofuranosidase enzyme to produce said fructooligosaccharides.

2. The process of claim 1, wherein the transfructosylation of the beta-fructofuranosidase enzyme is carried out in a solution with a pH ranging from 5.0 to 9.5.

3. The process of claim 1, wherein the transfructosylation of the beta-fructofuranosidase enzyme is carried out in a solution with a pH ranging from 6.0 to 8.5.

* * * * *